United States Patent [19]

Bak et al.

[11] Patent Number: 5,345,018
[45] Date of Patent: Sep. 6, 1994

[54] METHOD FOR PREPARING 1-CHLORO-1-IODOETHANE

[75] Inventors: Philip L. Bak, Amherst; Gregory P. Bidinger, Akron; Ross J. Cozens, Strongsville; Paul R. Klich, Lyndhurst, all of Ohio

[73] Assignee: The Geon Company

[21] Appl. No.: 35,017

[22] Filed: Mar. 22, 1993

[51] Int. Cl.$^5$ .............................................. C07C 17/08
[52] U.S. Cl. .................................... 570/249; 570/248
[58] Field of Search ................................ 570/248, 249

[56] References Cited

U.S. PATENT DOCUMENTS 3,983,187  9/1976  Moczgemba et al.
4,158,678  6/1979  Tatemoto et al.
4,243,770  1/1981  Tatemoto et al.
4,361,678  11/1982  Tatemodo et al.

OTHER PUBLICATIONS

Kharasch et al., IACS 56 pp. 712–714, 1934.
Otsu, "Living Radical Polymerization With Reduced Nickel/Halide Systems as a Redox Iniferter", Chemistry Express, vol. 5, No. 1D, pp. 801–804 (1990).
Oka, et al., "Vinylidene Fluoride-Hexafluoropropylene Copolymers Having Terminal Iodines", Contemporary Topics in Polymer Science, 1984, 4, pp. 763–777.
Logothetis, "Chemistry of Fluorocarbon Elastomers", Prog. Polymer Sci., vol. 14, 251–296, 1989.

*Primary Examiner*—Howard T. Mars
*Attorney, Agent, or Firm*—Helen Odar; Miles B. Dearth

[57] ABSTRACT

The present invention relates to a method of synthesizing 1-chloro-1-iodoethane by reacting hydrogen iodide with vinyl chloride monomer in the presence of an iodine containing catalyst under certain specified conditions. The resulting product of the reaction is a high yield, high purity 1-chloro-1-iodoethane. This 1-chloro-1-iodoethane is useful as a chain transfer agent in the polymerization of vinyl chloride monomer in a process which mimics a pseudo-living radical polymerization.

1 Claim, No Drawings

METHOD FOR PREPARING 1-CHLORO-1-IODOETHANE

BACKGROUND OF THE INVENTION

1. Related Application

This application is related to Ser. No. 08/034,981, entitled, "Method of Synthesizing Poly(Vinyl Chloride) By Means of a Pseudo-Living Radical Polymerization and Product Thereof" by Philip I. Bak, et. el. filed herewith.

2. Field of Invention

The present invention relates to a simple, efficient method of synthesizing 1-chloro-1-iodoethane. More particularly, the process of the present invention comprises the addition of substantially pure and anhydrous hydrogen iodide to vinyl chloride monomer in the presence of an iodine-catalyst. Under these conditions, the reaction results in 1-chloro-1-iodoethane. 1-Chloro-1-iodoethane is especially effective as an iodine containing chain transfer agent for the apparent pseudo-living polymerization of vinyl chloride in a process mimicking a living radical polymerization as explained in our copending application, referenced above. The 1-chloro-1-iodoethane chain transfer agent formed according to the method of the instant application can be added to a vinyl chloride polymerization system separately after the 1-chloro-1-iodoethane is formed. Alternatively, the 1-chloro-1-iodoethane may possibly be generated in the reaction vessel prior to the polymerization of the vinyl chloride monomer. By using 1-chloro-1-iodoethane prepared by the instant invention as a chain transfer agent during polymerization of vinyl chloride monomer, a poly(vinyl chloride) polymer having low molecular weight (Mn generally less than 30,000), low polydispersity (generally less than 2.2), and good thermal stability is formed as described in our copending application referenced above.

3. Description of the Art

The addition of hydrogen iodide to vinyl chloride was first described by Kharasch and Hannum in an article in 1934. The article, entitled "The Peroxide Effect in the Addition of Reagents to Unsaturated Compounds IV. The Addition of Halogen Acids to Vinyl Chloride", J. American Chem. Soc., 56, (1934) p. 712 described the addition of various halogen acids such as hydrogen iodide to vinyl chloride. In particular, Kharasch et. al. discuss the addition of 0.12 moles of hydrogen iodide to 0.1 mole of vinyl chloride in a reactor. By these experiments, Kharasch et. al. were studying the effects of peroxides on reactions which occur via a carbocation process as opposed to a free radical process.

An attempt was made to reproduce the work of Kharasch and Hannum under modern experimental conditions. Using the Kharasch procedure, there was no 1-chloro-1-iodoethane synthesized.

However, applicants have discovered a novel process for synthesizing 1-chloro-1-iodoethane. The 1-chloro-1-iodoethane is very useful as an iodine containing chain transfer agent in the polymerization of vinyl chloride as described in our copending application referenced above. A vinyl chloride polymer having good thermal stability along with low molecular weight and low polydispersity is formed using this chain transfer agent.

Accordingly, a primary object of the present invention is to synthesize 1-chloro-1-iodoethane.

Another object of the invention is to synthesize high purity 1-chloro-1-iodoethane.

Yet an additional object of the invention is to prepare 1-chloro-1-iodoethane for use as an iodine containing chain transfer agent which can be used during polymerization of vinyl chloride monomer in a process which mimics a living radical polymerization.

SUMMARY OF THE INVENTION

The foregoing and other objects, advantages and features of the invention may be achieved by the addition of substantially anhydrous hydrogen iodide to vinyl chloride monomer in the presence of an iodine catalyst in a reaction vessel under specified conditions. The resulting reaction yields 1-chloro-1-iodoethane which can be used as a chain transfer agent for the polymerization of vinyl chloride monomer. A polymer with low molecular weight, low polydispersity and good thermal stability is prepared using 1-chloro-1-iodoethane as a chain transfer agent during polymerization of vinyl chloride monomer in a process which mimics a living radical polymerization. The 1-chloro-1-iodoethane formed by the instant invention can be added separately to the vinyl chloride polymerization system or it is believed that this chain transfer agent can be formed in situ prior to the polymerization of the vinyl chloride monomer.

DETAILED DESCRIPTION OF THE INVENTION

This invention relates to the synthesis of high yield and high purity 1-chloro-1-iodoethane by the addition of anhydrous hydrogen iodide to vinyl chloride in the presence of an iodine catalyst in a reaction vessel under specified conditions. The resulting 1-chloro-1-iodoethane, which is generally at least ninety-five percent pure is useful as a chain transfer agent for the polymerization of vinyl chloride monomer. A poly(vinyl chloride) resin having a low molecular weight, low polydispersity and good thermal stability is prepared in a process which mimics a living radical polymerization using 1-chloro-1-iodoethane as a chain transfer agent.

The impact of the instant invention to the polymerization of vinyl chloride is significant because poly(vinyl chloride) is a unique and useful polymer. The uniqueness of this polymer lends to its versatility, usefulness, and adaptability in a variety of applications. Among a multitude of uses, poly(vinyl chloride) is resistant to both chemicals and moisture. Moreover, poly(vinyl chloride) can be formed into rigid articles and with the addition of plasticizer, into flexible articles. Poly(vinyl chloride) can be used in pipes, conduits, gaskets, electrical insulations, wire and cable jackets and containers, for example. However, its usefulness is impeded by the structural defects formed during the free radical polymerization process which is used to manufacture conventional poly(vinyl chloride). The free radical polymerization process at normal vinyl chloride polymerization temperatures generally does not yield low molecular weight, low polydispersity poly(vinyl chloride) having good thermal stability.

The use of 1-chloro-1-iodoethane formed by this invention is significant, because it (along with other iodine containing chain transfer agents) can transform the polymerization of vinyl chloride monomer into a controlled process which mimics a living radical polymerization process. 1-Chloro-1-iodoethane, formed by the instant invention as a chain transfer agent, easily and efficiently yields a poly(vinyl chloride) resin with a low molecular weight. Moreover, the use of 1-chloro-1-iodoethane as a chain transfer agent yields a poly(vinyl chloride) resin not only having low molecular weight, but also low polydispersity and good thermal stability as described in our above-referenced copending application.

The novel method of synthesis of 1-chloro-1-iodoethane of the instant invention can occur in any one of two possible ways. First, the 1-chloro-1-iodoethane can be synthesized separately, purified and used as desired. If used as a chain transfer agent during the pseudo-living radical polymerization of vinyl chloride monomer as disclosed in our co-pending application, Ser. No. 08/034,981, entitled "Method of Synthesizing Poly(Vinyl Chloride) by Means of a Pseudo-Living Radical Polymerization and Product Thereof", incorporated herein by reference, the 1-chloro-1-iodoethane formed by the instant process can be added at the beginning of polymerization or metered at a desired rate during the polymerization of the vinyl chloride monomer.

Alternatively, it is believed that the 1-chloro-1-iodoethane can be synthesized in the reaction vessel prior to the polymerization of vinyl chloride monomer by the addition of the appropriate quantity of hydrogen iodide and iodine catalyst to the vinyl chloride monomer already charged to the reaction vessel. The 1-chloro-1-iodoethane generated in the reactor would then be consumed during the course of the polymerization of vinyl chloride monomer via chain transfer reactions in a process which mimics a living radical polymerization.

The subject reagent of this invention is vinyl chloride. Preferably, the vinyl chloride should be of high purity and dryness. Moreover, a slight excess of vinyl chloride monomer over hydrogen iodide is recommended to ensure complete consumption of substantially anhydrous hydrogen iodide. The type and amount of vinyl chloride is within the ordinary skill of one in the art.

The hydrogen iodide is added to vinyl chloride monomer in a reactor in the presence of an iodine catalyst. The iodine catalyst can be any iodine containing compound which is capable of liberating molecular iodine and which will not in itself react with vinyl chloride or hydrogen iodide. The iodine catalyst can be an organic iodide, inorganic iodide or molecular iodine. The most preferred iodine catalyst is molecular iodine. Generally, 0.1 to 2 mole % catalyst is used. Preferably, 0.1 to 1 mole % is used.

The synthesis is carried out in any reaction vessel suitable for the reaction of vinyl chloride monomer and is within the scope of one of ordinary skill in the art. The reaction temperature is about $-75°$ C. to $100°$ C. Most preferably, the reaction temperature is about $-50°$ C. to $-45°$ C. The components react for approximately one to five hours in the reactor. Completion is indicated when the reactor pressure drops to the vapor pressure of the vinyl chloride. Using the instant method under specified conditions renders a yield in excess of 80 percent. The resulting 1-chloro-1-iodoethane may be purified as described below.

Iodine, which hinders vinyl chloride monomer polymerization, should be removed from the 1-chloro-1-iodoethane which is formed. If an organic iodide is used as catalyst for the reaction between vinyl chloride and hydrogen iodide, then the reaction product should be purified by distillation. If molecular iodine or an inorganic iodide is used as catalyst for the reaction between vinyl chloride and hydrogen iodide, then the 1-chloro-1-iodoethane may be purified simply by washing with sodium thiosulfate, followed by washing with water and finally drying the product over an anhydrous drying agent, e.g., magnesium sulfate. It is suggested that the 1-chloro-1-iodoethane should be stored in the dark over copper turnings to inhibit degradation.

EXAMPLES

EXAMPLE 1

A 1-liter three-necked flask, equipped with nitrogen ("$N_2$") purge, stirrer, and cold finger condenser was assembled. The flask was immersed in a dry ice/acetone bath and the cold finger filled with the same. The flask was flushed with $N_2$. 294.3 grams vinyl chloride monomer ("VCM") (4.71 moles) were slowly added from a vessel via Teflon tubing to the flask. The VCM condensed upon contact with the cooled flask walls. 105.2 grams hydrogen iodide ("HI") (0.82 moles) were slowly bubbled through the VCM via Teflon tubing. Then, approximately 3 grams (0.01 moles) iodine crystals were added. The contents of the flask were stirred at dry ice/acetone temperature for three hours and then the bath was removed. The cold finger was maintained for an additional two hours. Excess of the reagents were permitted to evaporate as the reaction mixture warmed to room temperature. 131.0 grams of the product were isolated as a purple liquid. The yield of 1-chloro-1-iodoethane was about 83.65%.

The purple liquid was found to lose its color in the presence of sodium thiosulfate. All of the liquid was added to a separatory funnel. An equal amount of 0.1N sodium thiosulfate was added. With continued shaking, a pale yellow organic layer (bottom layer) was obtained. The organic liquid was dried over magnesium sulfate.

Upon standing, the filtered material began to turn pink. Copper filings were added and two days later, the product was found to be a very pale yellow. A week later the color had not changed.

A 13-CNMR spectrum was run on the purified material in $CDCl_3$. Sharp, narrow peaks were found at 22.08 and 35.67 ppm. Very small peaks were found at approximately 85 and 130 ppm. The spectrum was identified as 1-chloro-1-iodoethane.

Comparative Example 2

The reaction was carried out in a 1 liter glass pressure vessel, equipped with an agitator according to the method of Kharasch and Hannum discussed above. The vessel was placed under an atmosphere of nitrogen. When the vessel was cooled to around $0°$ C., vinyl chloride monomer (125 grams, 2 moles) was added. With the temperature held at or below $0°$ C., approximately 245 grams (1.9 moles) of HI vapor were transferred into the vinyl chloride using a Teflon line. The colorless mixture of liquid was then stirred and the temperature allowed to warm to room temperature over a period of approximately four hours. During that time, the reaction mixture became a pale pink in color. On subsequent evaporation of excess reagents, no measurable yield of 1-chloro-1-iodoethane was obtained.

The fact that no 1-chloro-1-iodoethane was obtained using the Kharasch et. al. method reaffirms that Applicants' iodine containing catalyst is necessary to render 1-chloro-1-iodoethane.

From the foregoing description, one skilled in the art can easily ascertain the essential characteristics of this invention and without departing from the spirit and scope thereof can make various changes and modifications of the invention and adapt it to various usages and conditions.

We claim:
1. A process for preparing 1-chloro-1-iodoethane comprising combining substantially anhydrous hydrogen iodide and vinyl chloride monomer in the presence of from 0.1 to 2 mole % molecular iodine catalyst at a temperature of from about −75° C. to 100° C.

* * * * *